United States Patent [19]

Brossard et al.

[11] 4,210,641

[45] Jul. 1, 1980

[54] NOVEL POLYSACCHARIDE EXTRACTS AND METHOD OF USE

[75] Inventors: Claudine Brossard, Osny; Martine Henry, Fontenay le Fleury; Denis Raichvarg, Epinay sur Seine, all of France

[73] Assignee: Roussel Uclaf, Paris, France

[21] Appl. No.: 953,001

[22] Filed: Oct. 20, 1978

[30] Foreign Application Priority Data

Oct. 27, 1977 [FR] France .................... 77 32416

[51] Int. Cl.[2] ............... C08B 37/00; A61K 31/73
[52] U.S. Cl. ............................. 424/180; 424/89; 424/92; 536/1; 536/18
[58] Field of Search ............... 536/1, 18; 424/89, 92, 424/180

[56] References Cited

U.S. PATENT DOCUMENTS

| 3,314,801 | 4/1967 | Cadmus et al. | 536/1 |
|---|---|---|---|
| 3,438,915 | 4/1969 | Girard | 536/1 |
| 3,578,655 | 5/1971 | Konig et al. | 536/1 |
| 3,711,462 | 1/1973 | Abdo | 536/1 |
| 3,923,782 | 12/1975 | Finn et al. | 536/1 |
| 4,003,792 | 1/1977 | Mill et al. | 424/89 |

OTHER PUBLICATIONS

Myerowitz et al. "Chem. Abst.", vol. 81, 1974, p. 103,018p.

Primary Examiner—Johnnie R. Brown
Attorney, Agent, or Firm—Hammond & Littell, Weissenberger and Muserlian

[57] ABSTRACT

Novel polysaccharide extracts of microbial bodies of *Haemophilus influenza* having an apparent molecular weight greater than 200,000 and constituted principally of galactose, glucose and mannose having remarkable antigenic and immunostimulating activity with very good tolerance in warm-blooded animals and a process for their preparation.

12 Claims, No Drawings

NOVEL POLYSACCHARIDE EXTRACTS AND METHOD OF USE

STATE OF THE ART

Polysaccharide extracts of certain strains of *Haemophilus influenza* are described in the literature such as the article published in Journal of Immunology, Vol. 107, No. 4 (October 1971), p. 1070-1080 which describes the preparation of such polysaccharides from bacterial capsules of a serotype b *Haemophilus influenza* strain. According to the publication, the majority of the effects caused by *Haemophilus influenza*, in man as well as the infant, and notably in the case of meningitis is due to the presence of a toxin of a polysaccharide nature present in the capsules of serotype b *Heaemophilus influenza*. The object of the publication was to prepare a capsular extract and then to eliminate from the extract endotoxins and pyrogenic substances by deproteinization in order to discover a remedy for the said reactions.

To effect such a preparation, the authors sought to prepare in a predominate manner the capsular form of *Haemophilus influenze* in order to isolate the desired product. Schematically, the procedure was to treat with formaldehyde followed by precipitation with ethanol and then elution from a column. According to the indications reported in the article, the obtained polysaccharide was constituted by a polyribose phosphate possessing glycosidic bonds between the $C_1$ and $C_4$ atoms in the furanoside form of D-ribose and the product lacked toxic properties while maintaining antigenic properties and specific immunisant properties against *Haemophilus influenza*.

OBJECTS OF THE INVENTION

It is a object of the invention to provide novel polysaccharide extracts from microbial bodies of *Haemophilus influenza* and to provide a novel process for their preparation.

It is another object of the invention to provide novel antigenic and immunostimulating compositions and to provide a novel method of treating *Haemophilus influenza* infections in warm-blooded animals.

These and other objects and advantages of the invention will become obvious from the following detailed description.

THE INVENTION

The novel polysaccharide extracts of the invention are comprised of polysaccharide extracts of microbial bodies of *Haemophilus influenza* having an apparent molecular weight greater than 200,000 and constituted pricipally of galactose, glucose and mannose having remarkable antigenic and immunostimulating activity with very good tolerance in warm-blooded animals.

The apparent molecular weight is the molecular weight determined by means of a standarized porous gel using known macromolecular solutions. Examples of standarized porous gels acting as a molecular sieve are the commercial gels sold under the trademark Sephadex such as Sephadex G 200 gels and agarose gels (Sepharose 4B).

The polysaccharide expression consitutes principally galactose, glucose and mannose signifying that the polysaccharides contain about 40 to 50% of oses. Among the polysaccharides of the invention are notably polysaccharides characterized in that it contains also a small amount of osamines which is constituted by glucosamine.

The amount of osamines determined by the Elson Morgan method is on the order of 2% for the polysaccharides of the invention and the amount of the neutral oses such as galactose, glucose and mannose is on the order of 44.5% determined by the corrected Orcinol method. The products contain traces of migrant sugars by layer chromatography at the level of pentoses but do not contain heptoses or uronic acids or diaminopimelic acid. The absence of diaminopimelic acid from the polysaccharides indicates that there is no contamination by peptido-glycanes of the membrane cell wall.

Among the preferred polysaccharides of the invention are those obtained from the *Haemophilus influenza* strains deposited at Pasteur Institute in Paris under No. 52,151 and No. 5,481, especially No. 52,151. The strains belong to serotype a.

The novel process of the invention for the preparation of the polysaccharides comprises cultivating a microbial strain of *Haemophilus influenza* on a solid or liquid medium, harvesting the microbial bodies after complete development, extracting the washed microbial bodies with phenol, recovering the phenol phase and effecting a return to the aqueous phase to obtain an impure product, subjecting the latter to careful hydrolysis to obtain a purified product and removing combined fatty acids to obtain the desired polysaccharide.

The *Haemophilus influenza* strains are preferably cultivated in a stirred liquid medium under aerobic conditions. The culture medium used is that usually used for such strains and may for example contain meat extracts, caesin peptone, yeast autolysates, soya papainic peptone sugars, mineral elements, hemin, coenzyme I and distilled water.

To obtain the maximum yield of polysaccharides, the germs are recovered after complete development of microbial bodies or after about 6 hours at 37° C. and the microbial bodies are then washed. The phenolic extraction of the washed microbial bodies is effected with an aqueous phenolic solution at a temperature of about 65° C. The purification of the raw product consists of precipitation of nucleic acids with Streptomycin sulfate.

The Streptomycin sulfate present in the surnagent is advantageously eliminated by dialysis with a porous membrane which can be in the form of a shell of hollow fibers such as Hollow fiber $H_1DP_{10}$ fibers possessing a threshold retention of substances with a molecular weight greater than 10,000. The purified product is preferably subjected to lyophilisis. The careful hydrolysis is effected by heating in an aqueous organic solvent in the presence of an ion exchange resin.

The careful hydrolysis of the purified product is controlled by the Schwartzman reaction which is evidenced in rabbits by a non-specific local hypersensibility shown by an alteration of the endothelium of cutaneous vessels and a leucocytary infiltration of the wall of small vessels. The careful hydrolysis is preferably effected in refluxing aqueous chloroform in the presence of an ion exchange resin such as Dowex 50 W×8, 200 to 400 mesh H+ No. 41631. The careful hydrolysis is arrested when the Schwartzman becomes negative which under the test conditions becomes negative in about 15 hours. The resulting product is then preferably lyophilized.

The novel antigenic and immunostimulant compositions of the invention having very good tolerance are comprised of an antigenically and an immunostimulantly effective amount of a polysaccharide of the invention and an inert pharmaceutical carrier or excipient. The compositions may be in the form of tablets, dragees, gelules, granules, suppositories or injectable solutions or suspensions.

Examples of suitable excipients are talc, arabic gum, lactose, starch, magnesium stearate, cacao butter, aqueous or non-aqueous vehicles, fatty bodies of animal or vegetable origin, paraffinic derivatives, glycols, preservatives and diverse wetting agents, dispersants and emulsifiers.

The compositions are useful for the treatment or prevention of *Haemophilus influenza* infections, in the treatment or prevention of respiratory affections, of bronchitis and chronic bronchitis.

The novel method of treating or preventing *Haemophilus influenza* infections in warm-blooded animals, including humans, comprises administering to warm-blooded animals an antigenically and immunostimulatingly effective amount of a polysaccharide of the invention. The products may be administered orally, rectally, parenterally or locally. For example, an effective daily dose is 0.5 to 10 $\mu$g/kg when administered perlingually.

In the following examples there are described several preferred embodiments to illustrate the invention. However, it should be understood that the invention is not intended to be limited to the specific embodiments.

EXAMPLE 1

The pH of a nutritive medium consisting of 5 g of meat extracts, 5 g of sodium chloride, 5 g of casein peptone, 5 g of yeast autolysate, 3.5 g of bipotassium phosphate, 1.5 g of monopotassium phosphate, 20 g of soya papainic peptone and sufficient water for a total volume of 1000 ml was adjusted to 7.4 to 7.6 and the medium was sterilized. The medium was inoculated with a strain of *Haemophilus influenza* (Institute Pasteur Serotype No. 52,151) and then 10 g of glucose, 1 mg of hemin and 1.5 mg of coenzyme I were added thereto. The medium was held for 24 hours in an oven at 37° C. and the resulting inoculum was added to 10 liters of the above nutritive medium containing the same additives and the mixture was held at 37° C. in an oven for 16 hours. The resulting preculture was used to inoculate 80 liters of the above nutritive medium and then 800 g of glucose, 120 mg of hemin and 160 mg of coenzyme I were added thereto as well as 2.8 liters of a solution of the following composition: 1 liter of yeast extract, 400 g of glucose in 1 liter of water and sufficient water for a final volume of 10 liters with a pH of 8. The fermenter was allowed to stand for 6 hours and was then centrifuged at 30,000 rpm to obtain 130 g of moist germs.

100 g of the moist germs were added to 870 ml of exchanged water heated to 68° C. and 870 ml of 90% phenol heated to 68° C. The mixture was stirred at 2000 rpm and was then allowed to stand at 68° C. for 30 minutes. The mixture was then held at 4° C. for 12 hours and the phenol-water phases were separated by continuous centrifugation in a Westphalia centrifuge. The aqueous phase was clarified and the phenol phase was extracted again by addition of the sludge from the preceding centrifugation step and exchanged water to obtain the same volume as the first extraction. The mixture was again stirred for 30 minutes at 68° C., stood for 12 hours at 4° C. and was centrifuged as before. The combined aqueous phases were subjected to dialysis for 4 days to eliminate phenol and after the disappearance of phenol, the combined aqueous phases were concentrated to a volume of 3.5 liters with an Amicon membrane ($H_1DP_{10}$ membrane possessing a threshold retention of substances with a molecular weight greater than 10,000). The aqueous phase was centrifuged at 4° C. for 20 minutes at 12,000 rpm and was then lyophilized to obtain 6 g of a raw product in the form of a floculated white powder.

To purify the product, 240 ml of a solution of 2.5% streptomycin sulfate were slowly added over 45 minutes with active stirring to 1200 ml of a solution containing 5 mg/ml of the raw product and nucleic acids precipitated. The mixture stood for 15 minutes and was then centrifuged at 4° C. for 20 minutes at 12,000 rpm. The surnageant aqueous phase was subjected to dialysis with a porous membrane (hollow fiber shell $H_1DP_{10}$) with a threshold retention of substances with a molecular weight greater than 10,000 to remove streptomycin sulfate and the aqueous phase was lyophilized to obtain 1.3 g of purified product.

Analysis: %C 40.26 %H 6.84 %N 6.53 content of 9.5% proteins (Lowry methanol); 41% of neutral monosaccharides (orcinol method); 35% of neutral monosaccharides (corrected orcinol method); 6.8% of uronic acids (corrected carbazol); 5.6% of osamines (Elson Morgan method); and 1% of pentoses (Bial method).

For hydrolysis, the 1.3 g of purified product was dissolved in 650 ml of water and the solution was stirred at 4° C. for 12 hours and then was centrifuged for 20 minutes. The surnageant was added to 650 ml of chloroform and 310 g of Dowex resin 50 W×8-200-400 mesh H+ and the mixture was drained through a buchner funnel. The mixture was refluxed for 15 hours (temperature necessary to obtain a Schwartzman reaction or not) and the chloroform was removed by concentration at 40° C. under reduced pressure. The aqueous phase was hyophilized to obtain 0.65 g of polysaccharide extract of microbial bodies of *Haemophilus influenzae*.

Analysis: %C 40.02 %H 6.53 %N 0.90 content of 1% of proteins (Lowry method); 44.5% of neutral oses (corrected orcinol method); 0% of uronic acids (corrected carbazol); 2% of osamines (Elson Morgan method); 0.8% of pentoses (Bial method); and 0% of heptoses (Dische method). No diaminopimelic acid was found. The neutral oses were identified as galactose, glucose and mannose by chromatography with cellulose acetate, silica gel, paper. Identification of the osamine by electrophoresis showed the presence of glucosamine.

EXAMPLE 2

Sublingual tablets were prepared containing 25 $\mu$g of the polysaccharides of Example 1 in sufficient excipient of gum, tragacanth, lactose, talc, starch and magnesium stearate to obtain a final weight of 100 mg.

An injectable solution was prepared containing 25 $\mu$g of the polysaccharides of Example 1 in sufficient isotonic water to obtain a final volume of 2 ml.

PHARMACOLOGICAL DATA

A. Determination of antigenic activity

The antigenic activity of the polysaccharides of Example 1 was determined against a type of anti-*Haemophilus influenza* serum by classic tests used in immunology, namely the "ring test", by passive hemagglutination, by agglutination of germs, by the technique of Ouchterlony and by establishment of a precipitation curve. In these tests, the product of Example 1 showed a passive hemagglutination titer of 1/128 and 1/256.

B. Immunogenic power

Groups of 6 Fauve de Bourgogne rabbits were used in this test with each group receiving intercostally and intraveinously a dose of the product of Example 1 at 1, 10 and 100 µg/kg. One series of rabbits received the product of Example 1 without adjuvant and another group was immunized with the product of Example 1 plus a Freund complete adjuvant. The injection of the product was made for 30 days and samples of the blood were taken at days 0, 38, 47,74, 76, 101, 105 and 130. The presence of specific antibodies was detected beginning the 38th day and increased after the adjustment, the titers of hemagglutination found after this immunization being given 1/128 and 1/256. The serums were studied by the techniques of "ring test", of agglutination and quantitative precipitation. No difference was noted between the animals vaccinated with the product of Example 1 only and those vaccinated with the product of Example 1 and the Freund adjuvant.

C. Opsonins

This test determined by a colormetric method the aptitude by leucocytes to phagocyter of bacteria. It was assumed at the time of this determination that 0% of opsonization is equal to an optic density of 0.050 and that 100% opsonization is equal to a maximal optic density of 0.250. After having effected the calculations, it was found that the percentage of opsonization of the animals immunized with the products of Example 1 varied between 50 and 70% (the control animals showing an opsonization percentage of 0%).

D. Bactericidal power of serum

The serum of rabbits immunized with the product of Example 1 was contacted with different dilutions of a *Haemophilus influenza* culture. After seeding with a gelose medium and culture, the number of living colonies was compared to the control rabbits:—rabbit before immunization—day 0 (positive control=0% mortality of bacteria)—serum of rabbit vaccinated with *Haemophilus influenza* germs (negative control=100% of mortality). There was noted a very regular increase in the bactericidal power as a function of time:

| Day | % Mortality of bacteria |
|---|---|
| 0 | 0 |
| 38 | 0 |
| 47 | 0 |
| 52 | 80 |
| 74 | 75–80 |
| 76 | 75–80 |
| 101 | 83 |
| 130 | 100 |
| Control anti H-I serum | 100 |

This test shows the specific activity of the polysaacharide of the invention.

E. Neutralization of local endotoxinic activity

The product of Example 1 administered to rabbits antagonized by local *Haemophilus influenza* activity neutralized the activity of a product releasing a local activity (Schwartzman reaction).

F. Acute toxicity

The acute toxicity of the product of Example 1 was determined on groups of 10 mice and $LD_{50}$ (50% lethal dose) by intraperitoneal administration and was found to be between 65 and 110 mg/kg.

Various modifications of the products and processes of the invention may be made without departing from the spirit or scope thereof and it is to be understood that the invention is intended to be limited only as defined in the appended claims.

We claim:

1. Polysaccharide extracts of microbial bodies of *Haemophilus influenza* having an apparent molecular weight greater than 200,000 and constituted principally of galactose, glucose and mannose and containing a small amount of osamines.

2. A polysaccharide extracts of claim 1 wherein the osamine is glucosamine.

3. A polysaccharide extract of claim 1 wherein the *Haemophilus influenza* strain is selected from the group consisting of Pasteur Institute of Paris No. 52,151 and No. 5,481.

4. A polysaccharide extract of claim 3 wherein the strain is No. 52,151.

5. An antigenic and immunostimulatingly effective amount of a polysaccharide of claim 1 and an excipient.

6. A composition of claim 5 wherein the osamine is glucosamine.

7. A composition of claim 5 wherein the *Haemophilus influenza* strain is selected from the group consisting of Pasteur Institute of Paris No. 52,151 and No. 5,481.

8. A composition of claim 5 wherein the strain is No. 52,151.

9. A method of treating or immunizing against *Haemophilus influenza* infections in warm-blooded animals comprising administering orally, rectally, parenterally or topically to warm-blooded animals an antigenically and immunostimulatingly effective amount of a polysaccharide of claim 1.

10. A method of claim 9 wherein the osamine is glucosamine.

11. A method of claim 9 wherein the *Haemophilus influenza* strain is selected from the group consisting of Pasteur Institute of Paris No. 52,151 and No. 5,481.

12. A method of claim 9 wherein the strain is No. 52,151.

* * * * *